(12) United States Patent
Adair

(10) Patent No.: US 7,402,313 B2
(45) Date of Patent: Jul. 22, 2008

(54) METHOD FOR CONTROLLING PREECLAMPSIA AND ECLAMPSIA

(76) Inventor: Charles David Adair, 22 Mountain Orchard Path, Signal Mountain, TN (US) 37377

( * ) Notice: Subject to any disclaimer, the term of this patent is extended or adjusted under 35 U.S.C. 154(b) by 49 days.

(21) Appl. No.: 10/202,957

(22) Filed: Jul. 25, 2002

(65) Prior Publication Data
US 2004/0018201 A1    Jan. 29, 2004

(51) Int. Cl.
*A61K 39/395* (2006.01)
(52) U.S. Cl. .............. 424/133.1; 424/145.1; 424/158.1; 530/387.3; 530/388.24
(58) Field of Classification Search .............. 424/133.1, 424/130.1, 141.1, 175.1; 530/387.1
See application file for complete search history.

(56) References Cited

U.S. PATENT DOCUMENTS

| | | | |
|---|---|---|---|
| 4,767,720 A | 8/1988 | Lingwood | |
| 5,770,376 A | 6/1998 | Bagrov | |
| 6,290,657 B1* | 9/2001 | Adams et al. | 600/591 |
| 6,699,676 B1 | 3/2004 | Orlov et al. | |
| 6,835,715 B1 | 12/2004 | Valdes, Jr. et al. | |
| 2004/0133929 A1 | 7/2004 | Davisson | |
| 2005/0123999 A1 | 6/2005 | Valdes, Jr. et al. | |
| 2006/0263891 A1 | 11/2006 | Puschett | |

FOREIGN PATENT DOCUMENTS

| | | |
|---|---|---|
| WO | WO 2004/071273 | 8/2004 |
| WO | WO 2004/071273 A2 | 8/2004 |
| WO | WO 2004/071273 A3 | 8/2004 |

OTHER PUBLICATIONS

Adair et al. Elevated endotoxin-like factor complicating a multifetal second trimester pregnancy. 1996, Am. J. Nephrol. 16:529-531.*
The Merck Manual of Diagnosis and Therapy, 17th edition, 1999, Beers and Berkow, editors, Merck Research Laboratories, p. 2057-2058.*
Product Information Insert for Digibind (GlaxoSmithKline) Digoxin Immune FAB (Ovine) 2001, p. 1-8.*
Webster's New World Dictionary, third college edition, editor V. Neufeldt, Simon and Schuster, Inc., 1988, p. 68.*
Adair, D. et al.: Effects of Fab Digozin-Specific Antibody (Fab) On Mean Arterial Pressure (MAP) in Severe Preclampsia (PE) AJH 1997, pp. 10:11A-12A.
Goodlin, R.C.: Will Treatment With Digoxn Antibody Benefit Pregnant Patients With Toxemia and Elevated Digoxin Like Factor? Medical Hypotheses, 1987, vol. 24(1), pp. 107-110.
Adair, D. et al.: Elevated Endoxin-Like Factor Complicating a Multifetal Second Trimester Pregnancy: Treatment Digoxin-Binding Immunoglobulin; Am. J. Nephrol 1996, vol. 16, pp. 529-531.
Goodlin, R.C.: Antidigoxin Antibodies in Eclampsia, The New England Journal of Medicine, 1988, pp. 518-519.
Miyagi H, Higuchi M, Nakayama M, et al. Ouabain-Like Na+,K=-ATPase Inhibitory Activity of a Plasma Extract in Normal Pregnancy and Pregnancy Induced Hypertension, Japan J Pharmacol 1991: 57:571-581.
Beyers AD, Odendaal HJ, Spruyt LL, Parkin DP. The Possible Role of Endogenous Digitalis-Like Substance in the Causation of Pre-Eclampsia, SA Medical Journal 1984: 65:883-885.
Lopatin DA Ailamazian EK, Dmitrieva RI, et al. Circulating Bufodienolide and Cardenolide Sodium Pump Inhibitors in Preeclampsia, J Hypertens 1999: 17:1179-1187.
Craig RH, Knight A, Valdes R. Binding of Endogenous Digoxin-Like Immunoreactive Factor to Serum Proteins During Normal and Hypertensive Pregnancy, J Clin Immunoassay 1991: 14:245-250.
Ghione S, Balzan S, Decollogne S, et al. Endogenous Digitalis-Like Activity in the Newborn. J Cardiovasc Pharmacol 1993; 22(Suppl. 2):25-28.
Adair D, Wang Y, Lewis D, et al. Digoxin Binding Fragment Immunoglobulin Antibody (Digibind DFAB) Inhibits Thromboxane Production in Preeclamptic Placentas, Hypertension in Pregnancy 2000: 19(1):57 (Abstract).
Product Information Insert for DigiFab, Nov. 2001.
protherics.com/products/antibody.htm, Jan. 21, 2003.
Clinical Product Monograph for DigiFab final release, Feb. 4, 2002.
Product Information for Digiband, Aug. 2001.
Crossey, Michael J et al.; "Effects of Digoxin-Like Immunoreactive Substance and Digoxin FAB Antibodies on the New Digoxin Microparticle Enzyme Immunoassay", Therapeutic Drug Monitoring, vol. 19, No. 2, 1997, pp. 185-190.
Krep Hennig et al.; "Volume Sensitive Hypertension and the Digoxin-Like Factor: Reversal by a FAB Directed Against Digoxin in DOCA-Salt Hypertensive Rats." American Journal of Hypertension, vol. 8, No. 9, 1995, pp. 921-927.

(Continued)

*Primary Examiner*—G. R. Ewoldt
*Assistant Examiner*—Michael Szperka
(74) *Attorney, Agent, or Firm*—Hunton & Williams LLP

(57) ABSTRACT

A method of controlling preeclampsia includes the steps of providing a supply of digoxin immune Fab (ovine), calculating an appropriate dosage of the digoxin immune Fab (ovine) based on a patient's weight and using an assumed endogenous digitalis-like factor level, administering the appropriate dosage as an intravenous bolus, and repeating the administration of the appropriate dosage on a fixed schedule.

15 Claims, 1 Drawing Sheet

OTHER PUBLICATIONS

Ghione S. et al.; "Endogenous Digitalis-Like Activity in the Newborn" Journal of Cardiovascular Pharmacology, vol. 22, No. Suppl. 2, 1993, pp. S25-S28.

Goto A et al.; "Ouabain-Like Factor." Current Opinion in Nephrology and Hypertension, United States Mar. 1998, vol. 7, No. 2, pp. 189-196.

Baily Benoit.; "Are There Teratognic Risks Assoicated With Antidotes Used in the Acute Management of Poisoned Pregnant Women?", Birth Defects Research, vol. 67, No. 2, Feb. 2003, pp. 133-140.

M. Johansson et al., "Activity and Protein Expression of Na+/K+ ATPase Are Reduced in Microvillous Syncytiotrophoblast Plasma Membranes Isolated from Pregnancies Complicated by Intrauterine Growth Restriction", J. Clin. Endocrinol Metab., Jun. 2003, 88, (6), pp. 2831-2837.

Aizman, O. et al., "Ouabain, a steroid hormone that signals with slow calcium oscillations", *PNAS*, 2001, vol. 98, No. 23, pp. 13420-13424.

Amorium, M.M.R., et al., "Corticosteriod therapy for prevention of respiratory distress syndrome in severe preeclampsia", *Am. J. Obstet. Gyngol.*, 1999, vol. 180, No. 5, pp. 1283-1288.

Bagrov, A. Y., et al., "Characterization of a Urinary Bufodienolide Na+, K+-ATPase Inhibitor in Patients After Acute Myocardial Infarction", *Hypertension*, 1998, vol. 31, pp. 1097-1103.

Ball, W. J. Jr. et al., "Isolation and Characterization of Human Monoclonal Antibodies to Digoxin", *The Journal of Immunology*, 1999, vol. 163, pp. 2291-2298.

Butler, V. et al., "Digoxin-Specific Antibodies", *Proc. Natl. Acad. Sci. USA (Physiology)*, 1967, vol. 57, pp. 71-78.

Dasgupta, A. et al, "Monitoring Free Digoxin Instead of Total Digoxin in Patients with Congestive Heart Failure and High Concentrations of Dogoxin-like Immunoreactive Substances", *Clin. Chem.*, 1990, vol. 36, No. 12, pp. 2121-2123.

"Deaths Associated with a Purported Aphrodisiac—New York City, Feb. 1993-May 1995", *Morbidity and Mortality Weekly Report*, 1995, vol. 44, No. 46, pp. 853-861.

Dimitrieva, R.I. et al., "Cardiotonic Steroids: Potential Endogenous Sodium Pump Ligands with Diverse Function", *Exp. Biol. Med.*, 2002, vol. 227, No. 8, pp. 561-569.

Doris, P.A. et al., "Endogenous Sodium Pump Inhibitors and Blood Pressure Regulation: An Update on Recent Progress", *Proc. Soc. Exp. Biol. Med.*, 1998, vol. 218, pp. 156-167.

El-Masri, M.A. et al., "Human Adrenal Cells in Culture Produce Both Ouabain-like and Dihydroubain-like Factors", *Clin. Chem.*, 2002, vol. 48, No. 10, pp. 1720-1730.

Eddleston, M. et al., "Management of acute yellow oleander poisoning", *Q. J. Med.*, 1999, vol. 92, pp. 483-485.

Fedorova, O.V. et al., "Marinobufagenin, and Endogenous $\alpha$-1 Sodium Pump Ligand, in Hypertensive Dahl Salt-Sensitive Rats", *Hypertension*, 2001, vol. 37 part 2, pp. 462-466.

Fedorova, O.V. et al., "Endogenous Na,K Pump Ligands Are Differentially Regulated During Acute NaCl Loading of Dhal Rats", *Circulation*, 2000, vol. 102, pp. 3009-3014.

Federova, O.V. et al., "Endogenous Ligand of $\alpha_1$ Sodium Pump, Marinobufagenin, Is a Novel Mediator of Sodium Chloride-Dependent Hypertension", *Circulation*, 2002, vol. 105, pp. 1122-1127.

Federova, O.V. et al., "Antibody to marinobufagenin lowers blood pressure in pregnant rates on a high NaCl intake", *J. Hypertension*, 2005, vol. 00, No. 00, pp. 1-9.

Gonzalez, A. R. et al., "Digoxin-like immunoreactive substance in pregnancy", *AM. J. Obstet. Gynecol.*, 1987, vol. 157, pp. 660-664.

Goto, A. et al., "Putative Roles of Ouabainlike Compound in Hypertension: Revisited", *Hypertens. Res.*, 2000, Supp. 23, pp. S7-S13.

Gottlieb, S.S. et al., "Elevated Concentration of Endogenous Ouabain in Patients with Congestive Heart Failure", *Circulation*, 1992, vol. 86, No. 2, pp. 420-425.

Di Grande, A. et al., "Release of a Substance from the Human Placenta Having Digoxin-Like Immunoreactivity", *Clin. Exp. Pharmacol. Physiol.*, 1993, vol. 20, pp. 603-607.

Graves, S.W. et al., "An endogenous Ouabain-Like Factor Associated with Hypertensive Pregnant Women", *J. Clin. Endocrinol. Metabl.*, 1984, vol. 59, pp. 1070-1074.

Gusdon, J. P. Jr. et al., "A digoxin-like immunoreactive substance in preeclampsia", *Am. J. Obstet. Gynecol.*, 1984, vol. 150, pp. 83-85.

Goodlin, R. C. et al., "Fetal Endoxins and Complications of Pregnancy", *West. J. Med.*, 1988, vol. 148, pp. 590-592.

Harwood, S. et al., "Development of enzyme immunoassay for endogenous ouabain-like compound in human plasma", *Clin. Chem.*, 1997, vol. 43, No. 5, pp. 715-772.

Hamlyn, J.M. et al., "Identification and characterization of a ouabain-like compound from human plasma", *Proc. Natl. Acad. Sci. USA*, 1991, vol. 88, pp. 6259-6263.

Huston, J. S. et al., "Protein engineering of antibody binding sites: Recovery of specific activity in an anti-gigoxin single-chain Fv analogue produced in *Escherichia coli*", *Proc. Natl. Acad. Sci. USA*, 1988, vol. 85, pp. 5879-5883.

Juhaszova, M. et al., "NA+ pump low and high ouabain affinity $\alpha$ subunity isoforms are differently distributed in cells", *Proc. Natl. Acad. Sci. USA*, 1997, vol. 94, pp. 1800-1805.

Kaide, J. et al., "Effects of Digoxin-Specific Antibody Fab Fragment (Digibind) on Blood Pressure and Renal Water-Sodium Metabolism in $\frac{5}{6}$ Reduced Renal Mass Hypertensive Rats", *Am. J. Hypertens.*, 1999, vol. 12, pp. 611-619.

Kawamura, A. et al., "On the structure of endogenous ouabain", *Proc. Natl. Acad. Sci. USA*, 1999, vol. 96, pp. 6654-6659.

Li, M. et al., "Hemodynamic Effects of the Fab Fragment of Digoxin Antibody (Digibind) in Corticotropin )ACTH)-Induced Hypertension", *Am. J. Hypertens.*, 1997, vol. 10. No. 3 part 1, pp. 332-336.

Lin, M. et al., "Detection of Endogenous Digitalis-like Immunoreactive Factors in Human Blood", *Proc. Natl. Sci. Council ROC Part B Life Sci.*, 1998, vol. 22, No. 3, pp. 129-135.

McMillen, G.A. et al., "Comparable Effects of Digibind and DigiFab in Thirteen Digoxin Immunoassays", *Clin. Chem.*, 2002, vol. 48, No. 9, pp. 1580-1584.

Menezes, J. C. et al., "Digoxin antibody decreases natriuresis and diluresis in cerebral hemorrhage", *Intens. Care. Med.*, 2003, vol. 23, pp. 2291-2296.

Melero CP, et al., A Short Review on Cardiotonic Steroids and Their Aminoguanidine Analogues, *Molecules*, 2000, vol. 5, pp. 51-81.

Middleton, D. A. et al., Structural insights into the binding of cardiac glycosides to the digitalis receptor revealed by solid-state NMR, *Proc. Natl. Acad. Sci. USA*, 2000, vol. 97, No. 25, pp. 13602-13607.

Morris, J.F. et al., "Ouabain-Sensitive Na+, K+-ATPase Activity in Toad Brain," *Comp. Biochem. Physiol.*, 1997, vol. 118A, No. 3, pp. 599-606.

Ochs, H.R. et al., "Reversal of Advanced Digitoxin Toxicity and Modification of Pharmacokinetics by Specific Antibodies and Fab Fragments", *J. Clin. Invest.*, 1977, vol. 60, pp. 1303-1313.

Phelps, S.J. et al., "The influence of gestational age and preeclampsia on the presence an dmagnitude of serum endogenous digoxin-like immunoreactive substance(s)", *Am. J. Obstet. Gynecol.*, 1988, vol. 158, pp. 34-39.

Poston, L. et al., "Serum digoxin-like substance in pregnancy-induced hypertension", *Clin. Sci.* (London), 1989, vol. 77, pp. 189-194.

Pridjian, G. et al., "Preeclampsia Part 2: Experimental and Genetic Considerations", *Obstet. Gynecol. Survey*, 2002, vol. 57, No. 9, pp. 619-634.

Pudek MR, et al., "Seven Different Digoxin Immunoassay Kits Compared with Respect to Interference by a Digoxin-Like Immunoreactive Substance in Serum from Premature and Full Term Infants", *Clin. Chem.*, 1983, vol. 29, No. 11, pp. 1972-1974.

Pudek MR, et al., "Effect of Assay Conditions on Cross Reactivity of Digoxin-Like Immunoreactive Substance(s) with Radioimmunoassay Kits", *Clin. Chem.* 1985, vol. 31, No. 11, pp. 1806-1810.

Pullen MA, et al., "Characterization of the Neutralizing Activity of Digoxin-Specific Fab Toward Ouabain-like Steroids", *J. Pharm. and Exp. Therapeutics* 2004, vol. 310, No. 10, pp. 319-325.

Qazza Hmam, et al., "Declycosylated Produced of Endogenous Digoxin-like Immunoreactive Factor in Mammalian Tissue", *J. Biol. Chem.* 1995, vol. 271, No. 15, pp. 8137-8737.

Qazzaz Hmam, et al., "Secretion of a Lacton-Hydrogenated Ouabain-like Effector of Sodium, Potassium-Adenosine Triphosphatase Activity by Adrenal Cells", *Endocrinology*, 2000, vol. 141, No. 9, pp. 3200-3209.

Rosen H, et al., "Cardiac Steroids Induce Recycling of the Plasma Membrane in Human NT2 Cells", *Molecular Biology of the Cell*, 2004, vol. 15, pp. 1044-1054.

Seely E.W., et al., "Markers of Sodium and Volume Homeostasis in Pregnancy-Induced Hypertension", *J. Clin. Endocrinol. Metabol.* 1992, vol. 74, No. 1, pp. 150-156.

Schoner W, "Endogenous Cardiac Glycodsides, a New Class of Steroid Hormones", *Eur. J. Biochem.* 2002, vol. 269, pp. 2440-2448.

Schlehuber S., et al., "Tuning Ligan Afinity, Specificity and Folding Stability of an Engineered Lipocalin Variant- a So-Called "anticalin"—Using a Molecular Random Approach", *Biophys. Chem.* 2002, vol. 96, pp. 213-228.

Smith T.W., "Ouabain-Specific Antibodies: Immunochemicla Properties and Reversal of $Na^+$/ $K^+$—Activated Adenosine Triphosphatase Inhibition", *J. Clin. Inves.*, 1972, vol. 51, pp. 1583-1593.

Therein A.G. et al., "Mechanisms of Sodium Pump Regulation", *Am J. Physiol. Cell Physiol.*, 2000, vol. 279, pp. C541-C566.

Valdes R, Jr. et al., "Protein binding of Endogenous Digoxin-immunoactive Factors in Human Serum and its Variation with Clinical Condition", *J. Clin. Endocrinol. Metabol.*, 1985, vol. 60, pp. 1135-1143.

Valdes R and Jortani SA. Monitoring of unbound digoxin in patients with antidigoxin antigen-binding fragments: a model for the future? *Clin. Chem.* 1998; 44(9):1883-I 885.

Vu HV, et al., "Involvement of Marinobufagenin in a Rat Model of Human Preclampsia", *Am J Nephrol.*, 2005, vol. 25, No. 5, pp. 520-528.

Way B.A., et al., "Vitros Digoxin Immunoassay Evaluated for Interference by Digoxin-like Immunoreactive Factors", *Clin. Chem.*, 1998, vol. 44, No. 6, pp. 1339-1340.

Wolfson R.G., et al., "Digoxin-like Inhibitors of Active Sodium Transport and Blood Pressue: The Current Status", *Kidney Intl.*, 1994, vol. 46, pp. 297-309.

PCT/IPEA/409—International Preliminary Report on Patentability, dated Mar. 21, 2005 for International Application No. PCT/US04/02802, 6 pages.

PCT/ISA/237—Written Opinion of the International Searching Authority, dated Nov. 22, 2004 for International Application No. PCT/US04/02802, 5 pages.

Ilekis, J.V. et al., "Preeclampsia—A Pressing Problem: An Executive Summary of a National Institute of Child Health and Human Development Workshop," *Reproductive Sciences*, 14(6):508-523 (Sep. 2007).

Dostanic-Larson, I. et al., "The highly conserved cardiac glycoside binding site of Na,K-ATpase plays a role in blood pressure regulation," *Publication of the National Academy of Sciences*, 102(44): 15845-15850 (Nov. 1, 2005).

Kaplan, J.H., "The sodium pump and hypertension: A physiological role for the cardia glycoside binding site of the NA,K-ATPase," *Publication of the National Academy of Sciences*, 102(44): 15723-15724 (Nov. 1, 2005).

Wagner, MD, L.K., "Diagnosis and Management of Preeclampsia," *American Family Physician*, 70(12): 2317-2324 (Dec. 15, 2004).

"Diagnosis and management of preeclampsia and eclampsia," *American College of Obstetricians and Gynecologists Practice Bulletin No. 33*, 9 pages (Jan. 2002).

Schroeder, B.M., "Practice Guidelines: ACOG Practice Bulletin on Diagnosing and Managing Preeclampsia and Eclampsia," *American Family Physician®* 66(2) (Jul. 15, 2002).

Steier, MD, J.A. et al., "Human Chorionic Gonadotropin and Testosterone in Normal and Preeclamptic Pregnancies in Relation to Fetal Sex," *Obstetrics and Gynecology*, 100(3): 552-556 (Sep. 2002).

Bailey, B., Are There Teratogenic Risks Associated with Antidotes Used in the Acute Management of Poisoned Pregnant Women?, *Birth Defects Research* (Part A) 67:133-140 (2003).

Crossey, M.J. and Dasgupta, A., "Effects of Digoxinlike Immunoreactive Substances and Digoxin FAB Antibodies on the New Digoxin Microparticle Enzyme Immunoassay," *Therapeutic Drug Monitoring*, 19(2): 185-190 (1997).

Digibind® Product Information Sheet (Digibind® Digoxin Immune FAB (Ovine)) Distributed by GlaxoSmithKline, Research Triangle Park, NC 27709 (Aug. 2001).

DigiFab™ Digoxin Immune FAB (Ovine) Package Insert, U.S. License No. 1575 (Aug. 3, 2001).

DiGrande, A. et al., "Release of a Substance from the Human Placenta Having Digoxin-like Immunoreactivity," *Clinical and Experimental Pharmacology and Physiology* 20: 603-607 (1993).

Goto, A. and Yamada, K., "Ouabain-like Factor," *Curr Opin Nephrol Hypertens* 7: 189-196 (1998).

Johansson, M. et al., "Activity and Protein Expression of $Na^+$ /$K^+$ ATPase Are Reduced in Microvillous Syncytiotrophoblast Plasma Membranes Isolated from Pregnancies Complicated by Intrauterine Growth Restricton," *J Clin Endocrinol Metab*, 88(6): 2831-2837 (Jun. 2003).

Kaide, J. et al., "Effects of Digoxin-Specific Antibody Fab Fragment (Digibind) on Blook Pressure and Renal Water-Sodium Metabolism in ⅚ Reduced Renal Mass Hypertensive Rats," *Am J Hypertension* 12:611-619 (1999).

Kawamura, A. et al., "On the structure of endogenous ouabain," *Proc. Natl. Acad. Sci. USA* vol. 96: 6654-6659 (Jun. 1999).

Krep, H. et al., "Volume Sensitive Hypertension and the Digoxin-Like Factor: Reversal by a Fab Directed Against Digoxin in DOCA-Salt Hypertensive Rats," *Am J Hypertens* 1995;8:921-927.

Melero, C.P. et al., "A Short Review on Cardiotonic Steroids and Their Aminoguanidine Analogues," *Molecules*, 5: 51-81 (2000).

"Morbidity and Mortality Weekly Report," *U.S. Department of Health and Human Services, Center for Disease Control*, 44(46): 849-868 (Nov. 24, 1995).

Repke, J.T. et al., "Hypertension in pregnancy and preeclampsia. Knowledge and clinical practice among obstetrician-gynecologists," *Journal of Reproductive Medicine*, 47(6):472-476 (Jun. 2002).

Protherics PLC Press Release, "Release from phase 2b 'DEEP' study in severe pre-eclampsia," London, United Kingdom; Brentwood, Tennessee, United States of America (Apr. 22, 2008).

* cited by examiner

METHOD FOR CONTROLLING PREECLAMPSIA AND ECLAMPSIA

TECHNICAL FIELD OF THE INVENTION

The present invention relates generally to the field of medicine and, more particularly, to a method of controlling preeclampsia and eclampsia.

DESCRIPTION OF THE RELATED ART

Preeclampsia is a rapidly progressive condition occurring during pregnancy characterized by high blood pressure, swelling and protein in the urine. It is specifically defined as the presence of hypertension or pregnancy-induced hypertension ("PIH") accompanied by proteinuria, edema, or both after 20 weeks gestation. Preeclampsia occurs in 5 to 10 percent of all pregnancies and is most common in first-time pregnancies or in first pregnancies with a new partner or husband. Typically, preeclampsia occurs in the late second or third trimesters of pregnancy. Complications of preeclampsia include eclamptic seizures, hemolysis, elevated liver function tests, low platelet count (HELLP) syndrome, hepatic rupture, DIC pulmonary edema, acute renal failure, placental abruption, intrauterine fetal demise (IUFD), cerebral hemorrhage, cortical blindness, and retinal detachment.

Preeclampsia causes vasospasm, which constricts and damages the smooth lining of the blood vessels. This leads to the accumulation of platelets in the damaged blood vessels, which form small clots along the blood vessel wall and further narrow the blood vessel. This damage to blood vessels can also lead to edema, including cerebral edema. Vasospasm can occur throughout the body, damaging the heart, kidneys and liver. Vasospasm can also develop in the placenta, decreasing the blood supply to the fetus.

Preeclampsia is divided into mild and severe forms. Mild preeclampsia is indicated where the patient exhibits hypertension, a proteinuria level of greater than 300 mg per 24 hour period, mild edema signaled by weight gain of greater than 2 pounds per week or 6 pounds per month, and urine output of less than 500 ml per 24 hour period. Severe preeclampsia is indicated where the patient's blood pressure is greater than 160/110 on two occasions at least six hours apart while on bed rest or a systolic blood pressure increase of greater than 60 over a baseline value or a diastolic increase of greater than 30. In addition, a proteinuria level of greater than 5 g per 24 hour period or a reading of 31 or 41 on a urine dipstick, massive edema, oliguria (less than 400 ml per 24 hour period), presence of fetal growth retardation (IUGR), or systemic symptoms including pulmonary edema, headaches, visual changes, right upper quadrant pain, elevated liver enzymes or thrombocytopenia.

After a diagnosis of preeclampsia, the baby is generally induced and delivered if it is near term, i.e., after 36 weeks. However, if preeclampsia occurs earlier in the pregnancy, its impact is more profound. The only "cure" for the disease is delivery of the baby, which is generally contrary to the best interests of the baby if it is not near term. However, if the condition does not respond to traditional management options, early delivery may be the only option remaining. Traditional management includes bed rest, antihypertensive therapy, including methyldopa (Aldomet®), atenolol, and labetalol. If pregnancy from the diagnosis of preeclampsia to delivery could be extended relatively safely for both the fetus and mother, then significant improvement in perinatal outcomes may be achieved.

While the cause of preeclampsia and eclampsia remains unknown, several theories have been propounded. One theory proposes that elevated serum digoxin-like immune factors, a sodium/potassium ATPase enzyme inhibitor, play a central role in the increased peripheral vasoconstriction. This is thought to be mediated through ion exchange pumps resulting in increased intracellular calcium which promotes vasoconstriction and resultant hypertension. Based on this theory, it has been suggested that the use of digoxin immune Fab (ovine) may be productive in controlling preeclampsia and eclampsia and extending pregnancy.

Digoxin immune Fab (ovine), which is marketed in the United States as DIGIBIND® by GlaxoSmithKline and DIGIFAB™ by Protherics, Inc., is a sterile lyophilized powder of antigen binding fragments (FAB) derived from specific antidigoxin antibodies raised in sheep. Digoxin immune Fab (ovine) is indicated for treatment of digoxin or digitoxin overdose manifested by severe ventricular arrhythmias such as ventricular tachycardia or ventricular fibrillation, or progressive bradyarrhythmias such as severe sinus bradycardia or second or third degree heart block not responsive to atropine. DIGIBIND® is distributed in vials, with each vial containing 38 mg of digoxin-specific Fab fragments plus 75 mg of sorbitol as a stabilizer and 28 mg of sodium chloride and capable of binding approximately 0.5 mg of digoxin. DIGIBIND® is generally administered by intravenous injection after reconstitution with 4 mL/vial of sterile water for injection. DIGIFAB™ is distributed in 40 mg vials and contains no preservatives. DIGIFAB™ is generally administered by intravenous infusion over at least thirty minutes after reconstitution with 4 mL/vial of sterile water for injection.

While the use of digoxin immune Fab (ovine) in the treatment of preeclampsia and eclampsia has shown promise, a truly efficacious method of calculating suitable dosages of and administering the drug have eluded researchers in this field.

The present invention is directed to overcoming one or more of the problems set forth above.

SUMMARY OF THE INVENTION

An aspect of the present invention is to provide a method of controlling preeclampsia and eclampsia to extend pregnancy and allow further development of the fetus.

In accordance with the above aspect of the invention, there is provided a method of controlling preeclampsia or eclampsia that includes the steps of providing a supply of digoxin immune Fab (ovine), calculating an appropriate dosage based on a patient's weight and using an assumed endogenous digitalis-like factor level, administering the appropriate dosage as an intravenous bolus, and repeating the administration of the appropriate dosage on a fixed schedule.

These aspects are merely illustrative of the innumerable aspects associated with the present invention and should not be deemed as limiting in any manner. These and other aspects, features and advantages of the present invention will become apparent from the following detailed description when taken in conjunction with the drawings.

BRIEF DESCRIPTION OF THE DRAWINGS

Reference is now made more particularly to the drawings which illustrate the best presently known mode of carrying out the invention and wherein similar reference characters indicate the same parts throughout the views.

DETAILED DESCRIPTION

Figure 1:
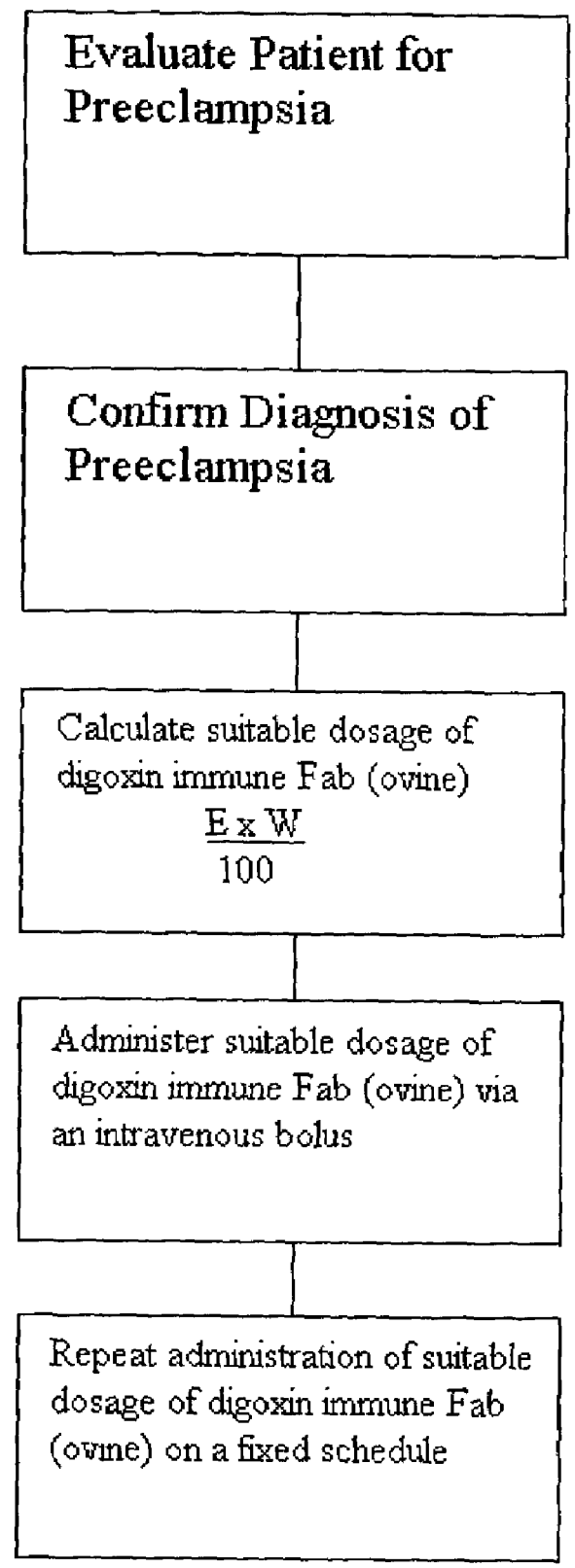
FIG. 1 is a flow chart illustrating the steps and sequence of a method for controlling preeclampsia according to an embodiment of the present invention.

According to one embodiment, a patient is first evaluated for preeclampsia or eclampsia. Once a diagnosis of preeclampsia is confirmed, a suitable dosage of a digoxin immune Fab (ovine), such as DIGIBIND® or DIGIFAB™, is calculated. A typical manufacturer's recommended dosage formula for a known digitalis toxicity level (E) is:

$$\frac{D \times W}{100}$$

where (D) is the serum digoxin concentration is ng/mL and W is the patient's weight. However, in preeclampsia and eclampsia cases there is no known digitalis toxicity level. Therefore, according to the method, an assumed endogenous digitalis factor level is required for the calculation. In one embodiment, the assumed endogenous digitalis-like factor level (E) is between approximately 3.0 and 5.0 ng/mL. In a preferred embodiment, the endogenous digitalis-like factor level is approximately 4.0 ng/mL. The endogenous digitalis-like factor level is then used in the following equation:

$$\frac{E \times W}{100}$$

where E is the endogenous digitalis-like factor level. Use of the preferred endogenous digitalis-like factor level results in an equation of:

$$\frac{4.0 \text{ ng/mL} \times (W)}{100}$$

which in turn produces the suitable dosage of digoxin immune Fab (ovine).

Once the dosage is calculated, it is administered to the patient via an intravenous bolus. Administration of the calculated dosage via intravenous bolus is then repeated on a fixed schedule of every five to eight hours. In a preferred embodiment, the dosage is administered every six hours.

In another embodiment, the administration of digoxin immune Fab (ovine) is accompanied by an administration of corticosteroids, such as betamethasone, to stimulate the cells in the lungs of the fetus in preparation for breathing air and decrease the risk of brain hemorrhage and intestinal problems in the fetus. The corticosteroids are administered once at the time of admission and again in twenty-four hours.

The method will now be further illustrated with reference to the following non-limiting example.

BIOLOGICAL EXAMPLE

A 16-year-old 70 Kg primigravida at 29 weeks 5/7 days presented with a presumed diagnosis of eclampsia. Her prenatal course had been uncomplicated until the day of admission. Her past medical history was negative for chronic illness. The patient had complaints of scotomata, persistent headache, and reported seizure activity for two episodes prior to hospital arrival and one on the labor deck. Initial evaluation revealed an alert patient with obvious postictal behavior. Her blood pressure was elevated at 160/110's and otherwise stable vital signs. Physical examination revealed A-V nicking on funduscopic exam, 4+ edema of the lower extremities and obvious facial and upper extremity edema. Deep tendon reflexes were 3 plus with 2 beats of clonus. The remainder of the exam was within normal limits. Lab evaluation of the urine noted proteinuria on qualitative analysis of 2+ and a urine specific gravity of 1.025. Serum chemistry revealed hyperuricacidemia at 8.2, elevated creatinine of 1.0, BUN of 6, and otherwise normal electrolytes and liver enzymes. The complete blood count revealed a platelet count of 429,000, white count of 10.4 and a hemoglobin/hematocrit of 12.0 and 35.6 respectively. The ammonia level was 3 and coagulation studies were normal. Urine drug screening was negative for substances of abuse including cocaine and methamphetamines. CT scanning of the maternal head failed to reveal any pathological abnormalities.

Ultrasound examination revealed a singleton gestation with a breech presentation. The estimated gestational age was consistent with the previously determined age of 29 weeks with an estimated fetal weight of 1331 grams. The amniotic fluid index was 5.42 cm and fetal breathing, movement, and tone were noted to be present. Doppler flow studies of the umbilical artery revealed an elevated S/D ratio of 5.6, RI of 0.82, and minimal diastolic flow. No anatomical abnormalities were noted on exam. Fetal cardiotocograph revealed a baseline of 135 with minimal beat-to-beat variability. Occasional non-repetitive decelerations were noted with good recovery. They were deemed to be non-ominous.

The patient was placed on intravenous magnesium sulfate. Central venous access and arterial line placement were performed. After informed discussion with the immediate family including the option to stabilize with compassionate off label use of fragmented antibody to digoxin and to administer corticosteroids for fetal benefit, the patient's mother provided consent.

Standard preeclampsia monitoring every hour was followed with ICU one on one nursing. Using an endogenous digitalis like factor level of 4.0 ng/mL and a dosage formula of 4.0 ng/mL×patient's body weight divided by 100 resulted in a dosage of 3 vials. This dosage was administered via an intravenous bolus and was repeated every 6 hours.

Intravenously administered fluids were standardized to 125 cc/hr. Urine output from admission to infusion was 300 cc over 6 hours. Over the first 6 hours post infusion the average urinary output was 100 cc with blood pressure readings of 148 to 162 systolic and 104 to 111 diastolic. At the next dosing interval the drug was doubled to 6 vials every six hours until 12 hours prior to delivery. Over the next 36 hours a diuresis followed over 5,840 cc of urine for an average hourly output of 162 cc. The total intake of intravenous fluids during the same time period was 3409 cc. The urine qualitative exam revealed negative proteinuria with a specific gravity of 1.011 and osmolality of 125, normal 500 to 800 mosm. Her creatinine decreased to 0.7 with the remainder of electrolytes remaining normal. Serial blood pressure measurements during the 36-hour period from the doubling of the dose ranged from 131 to 160 systolic (mean 140's) and diastolic 58 to 111 (mean 90's). The edema resolved in face and upper extremities with significant decreases in lower extremities as well to 1+. Deep tendon reflexes became 1+ with no clonus.

Fetal assessment during this time showed no changes in the cardiotocograph. Ultrasound examination every 6 hours revealed a reassuring biophysical score of 8 of 10. Doppler flow assessment of the umbilical artery every 6 hours revealed a decreasing S/D ratio with increasing diastolic component.

The S/D ratio 6 hours prior to delivery was 3.7 with a RI of 0.75 suggesting improved fetal hemodynamics albeit still abnormally elevated.

Cesarean delivery was performed at 48 hours post administration of corticosteroids secondary to a breech presentation. The delivery was attended by NICU and resulted in a livebirth of a female child. Apgars were 7 & 8 at one and five minutes respectively. The neonate did not require any oxygen support and was admitted to the NICU secondary to prematurity size of 1290 grams.

The maternal postoperative course was complicated by elevated blood pressures of 140 to 160's systolic and diastolic readings in the 100's. The patient was started on metoprolol 100 mg twice daily. She was discharged home on postoperative day #4 with stable blood pressures controlled with metoprolol. All follow up labs remained within normal limits. The neonate had no adverse sequelae and was discharged home on day of life #31.

Other objects, features and advantages of the present invention will be apparent to those skilled in the art. While preferred steps of the present invention have been illustrated and described, this has been by way of illustration and the invention should not be limited except as required by the scope of the appended claims and their equivalents.

I claim:

1. A method of extending pregnancy in a gravid human patient exhibiting at least one symptom of preeclampsia or eclampsia comprising administering a dosage of digoxin immune Fab (ovine) to the gravid human patient exhibiting at least one symptom of preeclampsia or eclampsia, wherein the dosage is calculated according to a formula of $(38 \text{ mg}) \times (E \times W)/100$, wherein E is between approximately 3.0 and 5.0 ng/mL, and W is the patient's weight in kilograms.

2. The method of claim 1, wherein E is approximately 4.0 ng/mL.

3. A method of extending pregnancy in a gravid human patient exhibiting at least one symptom of preeclampsia or eclampsia comprising:
   determining a dosage of digoxin immune Fab (ovine) according to a formula of $(38 \text{ mg}) \times (E \times W)/100$, wherein E is between approximately 3.0 and 5.0 ng/mL, and W is the patient's weight in kilograms; and
   administering said dosage to the gravid human patient exhibiting at least one symptom of preeclampsia or eclampsia.

4. The method of claim 3, wherein the E is approximately 4.0 ng/mL.

5. The method of claim 1, further comprising administering a subsequent dose of digoxin immune Fab (ovine), wherein the subsequent dose is determined by a calculation of two times the value obtained from said formula.

6. The method of claim 3, further comprising administering a subsequent dose of digoxin immune Fab (ovine), wherein the subsequent dose is determined by a calculation of two times the value obtained from said formula.

7. A method of extending pregnancy in a gravid human patient exhibiting at least one symptom of preeclampsia or eclampsia comprising administering a dosage of digoxin immune Fab (ovine) to a human patient according to a formula of 38 mg times an assumed level of an endogenous digitalis-like factor multiplied by the patient's body weight in kilograms divided by 100, wherein the assumed level of the endogenous digitalis-like factor is between 3.0 ng/mL and 5.0 ng/mL; and
   administering a subsequent dose of digoxin immune Fab (ovine), wherein the subsequent dose is determined by a calculation of two times the value obtained from said formula.

8. A method of extending pregnancy in a gravid human patient exhibiting at least one symptom of preeclampsia or eclampsia comprising the steps of:
   determining a dosage of digoxin immune Fab (ovine) by multiplying 38 mg times an assumed level of an endogenous digitalis-like factor times the patient's body weight in kilograms divided by 100, wherein the assumed level of the endogenous digitalis-like factor is between 3.0 ng/mL and 5.0 ng/mL;
   administering said dosage to a human patient; and
   administering a subsequent dose of digoxin immune Fab (ovine), wherein the subsequent dose is determined by a calculation of two times the value obtained from said formula.

9. A method of extending pregnancy in a gravid human patient diagnosed with preeclampsia or eclampsia comprising administering digoxin immune Fab (ovine) to the gravid human patient diagnosed with preeclampsia or eclampsia at a dosage in mg digoxin immune Fab (ovine) calculated according to a formula $(38 \text{ mg}) \times (E \times W)/100$, wherein E is between approximately 3.0 and 5.0 ng/mL, and W is the patient's weight in kilograms.

10. The method of claim 1, wherein the dosage is administered by an intravenous bolus.

11. The method of claim 1, wherein the dosage is administered by an intravenous bolus and repeated after six hours.

12. The method of claim 5, wherein each dosage is administered by an intravenous bolus.

13. The method of claim 3, wherein the dosage is administered by an intravenous bolus.

14. The method of claim 3, wherein the dosage is administered by an intravenous bolus and repeated after six hours.

15. The method of claim 6, wherein each dosage is administered by an intravenous bolus.

* * * * *